United States Patent
Watae et al.

(10) Patent No.: US 12,290,592 B2
(45) Date of Patent: May 6, 2025

(54) OILY MIXTURE COMPOSITION, COSMETIC, AND COSMETIC MANUFACTURING METHOD

(71) Applicant: SHIN-ETSU CHEMICAL CO., LTD., Tokyo (JP)

(72) Inventors: Seiji Watae, Tokyo (JP); Chihiro Hayakawa, Tokyo (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 787 days.

(21) Appl. No.: 17/600,188

(22) PCT Filed: Mar. 19, 2020

(86) PCT No.: PCT/JP2020/012294
§ 371 (c)(1),
(2) Date: Sep. 30, 2021

(87) PCT Pub. No.: WO2020/203351
PCT Pub. Date: Oct. 8, 2020

(65) Prior Publication Data
US 2022/0175652 A1    Jun. 9, 2022

(30) Foreign Application Priority Data
Apr. 1, 2019 (JP) .................. 2019-069822

(51) Int. Cl.
| | | |
|---|---|---|
| A61K 8/06 | (2006.01) | |
| A61K 8/02 | (2006.01) | |
| A61K 8/19 | (2006.01) | |
| A61K 8/29 | (2006.01) | |
| A61K 8/891 | (2006.01) | |
| A61Q 1/02 | (2006.01) | |
| A61Q 1/06 | (2006.01) | |

(52) U.S. Cl.
CPC ............ *A61K 8/891* (2013.01); *A61K 8/0229* (2013.01); *A61K 8/062* (2013.01); *A61K 8/064* (2013.01); *A61K 8/19* (2013.01); *A61K 8/29* (2013.01); *A61Q 1/02* (2013.01); *A61Q 1/06* (2013.01); *A61K 2800/43* (2013.01)

(58) Field of Classification Search
None
See application file for complete search history.

(56) References Cited

U.S. PATENT DOCUMENTS

| | | |
|---|---|---|
| 2014/0112965 A1 | 4/2014 | Nakamura et al. |
| 2017/0056624 A1 | 3/2017 | Bansal et al. |
| 2018/0133141 A1 | 5/2018 | Konishi et al. |
| 2020/0132579 A1 | 4/2020 | Inukai et al. |

FOREIGN PATENT DOCUMENTS

| | | | |
|---|---|---|---|
| EP | 1 416 016 A1 | 5/2004 | |
| EP | 1 772 138 A2 | 4/2007 | |
| EP | 2 357 024 A2 | 8/2011 | |
| JP | 2014-43422 A | 3/2014 | |
| JP | 2014-84251 A | 5/2014 | |
| JP | 2015-174844 A | 10/2015 | |
| JP | 2017-516591 A | 6/2017 | |
| WO | WO 2016/178380 A1 | 11/2016 | |
| WO | WO 2017/199732 A1 | 11/2017 | |
| WO | WO 2018/216722 A1 | 11/2018 | |
| WO | WO 2018/221174 A1 | 12/2018 | |
| WO | WO 2019/004048 A1 | 1/2019 | |
| WO | WO-2019044590 A1 * | 3/2019 | ........... A61K 8/0229 |

OTHER PUBLICATIONS

International Search Report for PCT/JP2020/012294 (PCT/ISA/210) mailed on Jun. 16, 2020.
Written Opinion of the International Searching Authority for PCT/JP2020/012294 (PCT/ISA/237) mailed on Jun. 16, 2020.
Extended European Search Report for corresponding European Application No. 20783264.3, dated May 12, 2023.

* cited by examiner

*Primary Examiner* — Susan T Tran
(74) *Attorney, Agent, or Firm* — Birch, Stewart, Kolasch & Birch, LLP

(57) ABSTRACT

Provided is a cosmetic wherein agglomeration during dispersion of a coloring pigment is suppressed, pigment irregularity in the bulk cosmetic and a coating film of the cosmetic is suppressed, and superior coloring pigment uniformity is demonstrated. An oily mixture composition including: (a) a silicone surfactant with an HLB of 6 or less; (b) an acrylic-silicone graft copolymer; (c) an oil that is liquid at 25° C.; and (d) a coloring pigment.

13 Claims, No Drawings

OILY MIXTURE COMPOSITION, COSMETIC, AND COSMETIC MANUFACTURING METHOD

TECHNICAL FIELD

This invention relates to an oily admixture, a cosmetic composition having the oily admixture blended therein, and a method of preparing the cosmetic composition.

BACKGROUND ART

By virtue of their coloring effect, coloring pigments are generally blended in makeup cosmetics for the purposes of beautifying, attractiveness, and appearance change. Specifically, inorganic coloring pigments include titanium oxide of white color and iron oxides of yellow, red and black colors. Thus, the technique of combining such pigments so as to adjust the color to the human skin color and to hide or cover skin troubles so that the skin looks beautiful and attractive is generally used in makeup cosmetics such as foundations.

On the other hand, since powders such as coloring pigments are liable to agglomerate together, the step of blending a powder in cosmetics employs the technique of improving the wettability or dispersion of the powder for improving the lasting quality or storage stability of cosmetics. For example, there are known techniques of improving the stability of preparations, using polyether-modified silicone surfactants (Patent Document 1: JP-A 2014-043422) and polyglycerin-modified silicone surfactants (Patent Document 2: WO 2016/178380).

One of the processes taken in the preparation of makeup cosmetics such as liquid foundations, involves the steps of previously dispersing titanium oxide and iron oxides of yellow, red and black colors in an oil with the aid of a surfactant as typified above, to form an oily admixture, and blending the oily admixture in a cosmetic composition. Even though dispersibility is enhanced using the surfactant, there is a possibility that the pigments are unevenly distributed in the cosmetic composition. The uneven distribution of pigments in a cosmetic composition detracts from aesthetic beauty and causes variations upon skin application. As used herein, the uneven pigment distribution refers to a local distribution of any coloring pigment visually perceivable in the bulk cosmetic composition or a coating of the cosmetic composition after application. In the case of a foundation, for example, red streaks due to segregation of red iron oxide or white streaks due to segregation of white titanium oxide in a bulk cosmetic composition of certain skin color are perceivable as the uneven pigment distribution. Also, where some areas of different color are surrounded by the bulk cosmetic composition of skin color like mist, these areas are perceivable as the uneven pigment distribution. Such uneven pigment distribution not only gives rise to problems in the bulk cosmetic composition, but also in actually applying the cosmetic composition to the skin, causes lines to be drawn on the skin by segregating pigment, makes it cumbersome to spread the pigment uniformly, and adversely affecting the appearance of a product.

PRIOR ART DOCUMENTS

Patent Documents

Patent Document 1: JP-A 2014-043422
Patent Document 2: JP-A 2017-516591 (WO 2016/178380)

SUMMARY OF INVENTION

Technical Problem

An object of the invention, which has been made under the above-mentioned circumstances, is to provide a cosmetic composition which is improved in the uniformity of coloring pigments and which is effective for preventing the coloring pigments from agglomerating during their dispersion, and eliminating uneven pigment distribution in the cosmetic composition in bulk and a coating thereof.

Solution to Problem

Making extensive investigations to attain the above object, the inventors have found that by previously dispersing a coloring pigment in an oil which is liquid at 25° C. with the aid of a silicone surfactant having low HLB and an acrylic silicone graft copolymer to form an oily admixture, and blending the admixture in a cosmetic composition, the cosmetic composition is drastically suppressed in uneven pigment distribution. The invention is predicated on this finding.

Accordingly, the invention is as defined below.
1. An oily admixture comprising
   (a) a silicone surfactant having an HLB value of up to 6,
   (b) an acrylic silicone graft copolymer,
   (c) an oil which is liquid at 25° C., and
   (d) a coloring pigment.
2. The oily admixture of 1 wherein a blending weight ratio of component (b) to component (a) in the oily admixture, represented by (b)/(a), is from 0.046 to 3, and a blending weight ratio of the sum of components (a) and (b) to component (d) in the oily admixture, represented by {(a)+(b)}/(d), is at least 0.02.
3. The oily admixture of 1 or 2 wherein component (a) is a polyglycerin-modified silicone surfactant.
4. The oily admixture of 3 wherein component (a) is a polyglycerin-modified silicone surfactant having an alkyl chain and/or silicone chain branching from a silicone backbone.
5. The oily admixture of any one of 1 to 4 wherein component (b) is an acrylate/ethylhexyl acrylate/dimethicone methacrylate copolymer (INCI name).
6. The oily admixture of any one of 1 to 5 wherein component (c) is at least one oil selected from hydrocarbon oils, ester oils, and silicone oils.
7. The oily admixture of any one of 1 to 6 wherein component (d) is a coloring pigment selected from titanium oxide and iron oxide.
8. The oily admixture of any one of 1 to 7 wherein component (d) is a coloring pigment which has been subjected to inorganic surface treatment or hydrophobic surface treatment.
9. The oily admixture of 8 wherein the inorganic surface treatment is a surface treatment with an inorganic surface treatment agent selected from alumina, aluminum hydroxide, and silica.
10. The oily admixture of 8 wherein the hydrophobic surface treatment is a surface treatment with a hydrophobic surface treatment agent selected from silicones, fluorine compounds, metal soaps, and amino acids.

11. A cosmetic composition having the oily admixture of any one of 1 to 10 blended therein.
12. The cosmetic composition of 11, further comprising (e) 1 to 10% by weight based on the cosmetic composition of an oily thickener having a melting point of at least 55° C.
13. The cosmetic composition of 11 or 12 which is a nonaqueous composition.
14. The cosmetic composition of any one of 11 to 13 which is an emulsified composition.
15. The cosmetic composition of 14 which is of water-in-oil or oil-in-water-in-oil type.
16. A method for preparing a cosmetic composition comprising the steps of:
   (I) mixing (a) a silicone surfactant having an HLB value of up to 6, (b) an acrylic silicone graft copolymer, (c) an oil which is liquid at 25° C., and (d) a coloring pigment to form an oily admixture, and mixing the oily admixture resulting from step (I) with another component.

Advantageous Effects of Invention

According to the invention, an oily admixture to be blended in a cosmetic composition is obtained. The cosmetic composition having the oily admixture blended therein is improved in uniformity in that the agglomeration of coloring pigments is restrained and uneven pigment distribution is eliminated.

DESCRIPTION OF EMBODIMENTS

Now the invention is described in detail. Some compound names are described by International Nomenclature of Cosmetic Ingredients (INCI) names, hereinafter.

I. Oily Admixture

[Component (a)]

Component (a) used herein is a silicone surfactant having an HLB value of up to 6, which helps to disperse component (d) in component (c) in a stable manner. Component (a) is not particularly limited as long as it is a surfactant of silicone skeleton (or polysiloxane structure) having an HLB value of up to 6. The surfactant may be used alone or in a suitable combination of two or more. As used herein, the HLB is measured by Griffin's method.

Of various surfactants as component (a), polyoxyalkylene-modified silicone surfactants and polyglycerin-modified silicone surfactants are preferred. In view of chemical structure, these modified silicones may be obtained by modifying the silicone chain or backbone with polyoxyalkylene and polyglycerin in block type or branched type. The modified silicones of branched type are preferred from the standpoint of keeping component (d) or coloring pigment highly dispersible, that is, maintaining the uniform dispersion of the coloring pigment in a cosmetic composition. On the other hand, in the chemical structure of silicone backbone, surfactants having a silicone chain and/or alkyl chain branching from a silicone backbone exert more effects.

Of these, polyglycerin-modified silicone surfactants having polyglycerin chain exert more effects. Especially, polyglycerin-modified silicone surfactants having an alkyl chain and/or silicone chain branching from a silicone backbone are preferred. Specifically, surfactants having a polyglycerin chain and silicone chain branching from a silicone backbone, and surfactants having a polyglycerin chain, silicone chain and alkyl chain branching from a silicone backbone are preferred.

Examples of the silicone surfactant having an HLB value of up to 6 include the following compounds, defined by INCI names:

PEG-10 dimethicone: KF-6017 (polyoxyethylene chain branching from silicone backbone), PEG-9 polydimethylsiloxyethyl dimethicone: KF-6028 (polyoxyethylene chain and silicone chain branching from silicone backbone), lauryl PEG-9 polydimethylsiloxyethyl dimethicone: KF-6038 (polyoxyethylene chain, silicone chain and alkyl chain branching from silicone backbone), cetyl PEG/PPG-10/1 dimethicone: KF-6048 (polyoxyalkylene chain and alkyl chain branching from silicone backbone), polyglyceryl-3 polydimethylsiloxyethyl dimethicone: KF-6104 (polyglycerin chain and silicone chain branching from silicone backbone), Lauryl polyglyceryl-3 polydimethylsiloxyethyl dimethicone: KF-6105 (polyglycerin chain, silicone chain and alkyl chain branching from silicone backbone), and polyglyceryl-3 polydimethylsiloxyethyl dimethicone: KF-6106 (polyglycerin chain and silicone chain branching from silicone backbone), all available from Shin-Etsu Chemical Co., Ltd.

The silicone surfactant may be blended in a cosmetic composition as an additional component other than the oily admixture as long as the benefits of the invention are not compromised. Particularly when the desired cosmetic composition is an emulsified composition, the silicone surfactant is preferably blended in the cosmetic composition as an additional component other than the oily admixture for emulsifying aqueous phase components and oil phase components.

The amount of component (a) blended is preferably 0.1 to 30% by weight, more preferably 0.8 to 22% by weight of the oily admixture, though not particularly limited.

Where component (a) is blended in a cosmetic composition as an additional component other than the oily admixture, the amount of component (a) blended (exclusive of the amount of component (a) in the oily admixture) is preferably 0.1 to 15% by weight, more preferably 0.1 to 5% by weight of the cosmetic composition.

[Component (b)]

Component (b) used herein is an acrylic silicone graft copolymer, which helps to disperse component (d) in component (c) in a stable manner. When component (b) is blended in combination with component (a), dispersibility is further improved, achieving a dramatic reduction of uneven pigment distribution. Any well-known acrylic silicone graft copolymers may be used alone or in suitable combination of two or more.

Typical of the acrylic silicone graft copolymer are graft copolymers having a dimethylpolysiloxane chain grafted to an acrylic polymer chain. Examples include the following compounds, defined by INCI names: acrylate/dimethicone copolymers, acrylate/stearyl acrylate/dimethicone methacrylate copolymers, acrylate/behenyl acrylate/dimethicone methacrylate copolymers, and acrylate/ethylhexyl acrylate/dimethicone methacrylate copolymers. Of these, acrylate/dimethicone copolymers and acrylate/ethylhexyl acrylate/dimethicone methacrylate copolymers are preferred, with acrylate/ethylhexyl acrylate/dimethicone methacrylate copolymers being more preferred. The acrylate/dimethicone copolymers are commercially available as a solution in a solvent under the trade name of KP-543, 545, 549, 550 and 545L from Shin-Etsu Chemical Co., Ltd., and the acrylate/ethylhexyl acrylate/dimethicone methacrylate copolymers are commercially available under the trade name of KP-578 from Shin-Etsu Chemical Co., Ltd.

The acrylic silicone graft copolymer may be blended in a cosmetic composition as an additional component other than the oily admixture as long as the benefits of the invention are not compromised. In particular, since the above-mentioned KP-543, 545, 549, 550 and 545L can also be blended in a cosmetic composition as a film former, the acrylic silicone graft copolymer is preferably blended in a cosmetic composition as an additional component when the cosmetic composition is desired to have a high film-forming ability.

The amount of component (b) blended is preferably 0.1 to 10% by weight, more preferably 0.5 to 2.5% by weight of the oily admixture, though not particularly limited.

Where component (b) is blended in a cosmetic composition as an additional component other than the oily admixture, the amount of component (b) blended (exclusive of the amount of component (b) in the oily admixture) is preferably 0.1 to 15% by weight, more preferably 0.1 to 5% by weight of the cosmetic composition.

[Component (c)]

Component (c) used herein is an oil which is liquid at 25° C. Component (c) is essential as a dispersing medium for component (d). The oil is not particularly limited as long as it is liquid at 25° C. Any oils which are commonly used in cosmetics may be used alone or in suitable combination of two or more. Inter alia, an oil which has high affinity to components (a) and (b) and high solubility relative to components (a) and (b) is preferred as component (c).

Examples of the oil which is liquid at 25° C. include plant oils such as olive fruit oil, jojoba seed oil, and macadamia seed oil; animal oils such as liquid lanolin; straight or branched hydrocarbon oils such as liquid paraffin, isododecane, isohexadecane, and squalane; fatty acid esters such as isotridecyl isononanoate; ester oils such as fatty acid esters of polyhydric alcohols; and silicone oils such as dimethylpolysiloxane, methylphenylpolysiloxane, octamethylcyclotetrasiloxane, decamethylcyclopentasiloxane, and dodecamethylcyclohexasiloxane. Of these, hydrocarbon oils, ester oils and silicone oils are preferred in view of high affinity and high solubility relative to components (a) and (b).

The oil which is liquid at 25° C. may be blended in a cosmetic composition as an additional component other than the oily admixture as long as the benefits of the invention are not compromised.

The amount of component (c) blended is preferably 5 to 80% by weight, more preferably 12 to 55% by weight of the oily admixture, though not particularly limited.

Where component (c) is blended in a cosmetic composition as an additional component other than the oily admixture, the amount of component (c) blended (exclusive of the amount of component (c) in the oily admixture) is preferably 5 to 90% by weight, more preferably 10 to 40% by weight of the cosmetic composition.

[Component (d)]

Component (d) used herein is a pigment which is blended for coloring purpose. Any pigments which are commonly used in cosmetics may be used alone or in suitable combination of two or more. Examples include inorganic coloring pigments such as zinc white, titanium oxide, red iron oxide, yellow iron oxide, black iron oxide, ultramarine, Prussian blue, carbon black, substoichiometric titanium oxide, cobalt violet, chromium oxide, chromium hydroxide, cobalt titanate, bismuth oxychloride, and titanium-mica based pearl pigment; and organic coloring pigments, typically zirconium, barium or aluminum lake pigments such as Red #202, Red #204, Red #205, Red #220, Red #226, Red #228, Red #405, Orange #203, Yellow #205, Yellow #4, Yellow #5, Blue #1, Blue #404, and Green #3. In particular, although titanium oxide and iron oxide are highly agglomerative and generally difficult to disperse, the invention enables effective dispersion of these pigments in a cosmetic composition.

The coloring pigment may be blended in a cosmetic composition in untreated state, that is, without surface treatment with another inorganic or organic composition while surface-treated coloring pigments which have been surface treated by any well-known methods used in cosmetics may also be used. The surface treatment encompasses inorganic surface treatments and hydrophobic surface treatments. Suitable inorganic surface treatment agents include alumina (aluminum oxide), aluminum hydroxide, and silica. Suitable hydrophobic surface treatment agents include silicones, fluorine compounds such as perfluoroalkyl phosphates, metal soaps such as aluminum stearate and magnesium myristate, and amino acids such as N-acylglutamic acid. Whether an inorganic surface treatment agent or an organic surface treatment agent is used as the surface treatment agent, the surface treatment agent is preferably fixed to the coloring pigment by electric or chemical bonds from the aspect of preventing the agent from separating from the pigment surface. Particularly for the purpose of imparting water repellency to the coloring pigment, the silicone treatment agent is preferably fixed to the coloring pigment surface by chemical bonds.

Suitable silicone treatment agents include methylhydrogen type polysiloxanes having a Si—H bond as reactive group (KF-99P, KF-9901, etc. by Shin-Etsu Chemical Co., Ltd.), caprylyl silanes having a metal alkoxide as reactive group (AES-3083 by Shin-Etsu Chemical Co., Ltd.), silicone-branched silicone treatment agents (KF-9908, KF-9909, etc. by Shin-Etsu Chemical Co., Ltd.), and silicone-modified acrylic treatment agents (KP-574 by Shin-Etsu Chemical Co., Ltd.). Especially, a coloring pigment treated with KF-9909 (Shin-Etsu Chemical Co., Ltd.) develops high water repellency. Titanium oxide, yellow iron oxide, red iron oxide, and black iron oxide powders treated with KF-9909 are commercially available under the trade name of KTP-09W, KTP-09Y, KTP-09R, and KTP-09B, respectively, from Shin-Etsu Chemical Co., Ltd.

The amount of component (d) blended is preferably 1 to 90% by weight, more preferably 8 to 85% by weight of the oily admixture, though not particularly limited. Although the coloring pigment may be blended in a cosmetic composition as an additional component other than the oily admixture as long as the benefits of the invention are not compromised, the amount of component (d) blended as an additional component other than the oily admixture (exclusive of the amount of component (d) in the oily admixture) is preferably 0 to 5% by weight of the cosmetic composition because uneven pigment distribution can be otherwise incurred due to poor dispersion or agglomeration.

In the oily admixture, one or more components other than components (a) to (d) may be blended insofar as the benefits of the invention is not compromised. The total amount of components (a) to (d) blended is preferably 40 to 100% by weight, more preferably 60 to 100% by weight, and even 100% by weight of the oily admixture.

A blending weight ratio of components in the oily admixture is as follows.

A blending weight ratio of component (b) to component (a) in the oily admixture, represented by (b)/(a), is preferably from 0.046 to 3, more preferably from 0.3 to 0.6 in view of dispersion of the coloring pigment.

A blending weight ratio of the sum of components (a) and (b) to component (d) in the oily admixture, represented by {(a)+(b)}/(d), is preferably at least 0.02, more preferably from 0.02 to 0.35, even more preferably from 0.04 to 0.06 in view of dispersion of the coloring pigment.

The method for preparing the oily admixture may be selected from well-known, commonly used methods and is not particularly limited. The following step (I) is exemplary.

Step (I) of mixing (a) a silicone surfactant having an HLB value of up to 6, (b) an acrylic silicone graft copolymer, (c) an oil which is liquid at 25° C., and (d) a coloring pigment to form an oily admixture Further, any optional components may be blended. Components (a) to (d) and optional components are mixed and dispersed. The mixing unit used herein is not particularly limited and may be selected from media agitating mills, dispersing mixers, ultrasonic dispersing mixers, and high-speed mixers. Inter alia, dispersion on a three-roll mill is preferred for versatility and simplicity.

The oily admixture is a dispersion of (d) a coloring pigment in (c) an oil which is liquid at 25° C. with the aid of combined use of (a) a silicone surfactant having an HLB value of up to 6 and (b) an acrylic-silicone graft copolymer. Particularly when it is mixed with another component to form a cosmetic composition, the amount of the coloring pigment (d) blended is preferably up to 30% by weight of the cosmetic composition in view of covering power and skin affinity. Also preferably, the oily admixture is substantially free of water. Specifically the water content is up to 1% by weight of the oily admixture, and even 0% by weight.

II. Cosmetic Composition

The invention also provides a cosmetic composition having the oily admixture blended therein. The amount of the oily admixture blended is not particularly limited. Although the oily admixture may be a cosmetic composition (100% by weight) as such, the amount of the oily admixture blended is preferably 0.1 to 60% by weight, more preferably 0.3 to 30% by weight of the cosmetic composition.

The form of the inventive cosmetic composition may be either an emulsified composition or a nonaqueous composition. The emulsified composition is selected when it is desired to impart a fresh feeling on use. The emulsion may be of either oil-in-water (O/W) type or water-in-oil (W/O) type, or even oil-in-water-in-oil (O/W/O) or water-in-oil-in-water (W/O/W) type. In particular, in the case of the water-in-oil (W/O) type emulsion which is susceptible to uneven pigment distribution because the hydrophobized coloring pigment is dispersed in the outer phase, the invention is more effective. Further, in the case of the solid water-in-oil (W/O) type emulsified composition, which must be adjusted to a low viscosity by melting in the preparation and filling steps, the invention is more effective to the uneven pigment distribution occurring at such low viscosity. As used herein, the "nonaqueous composition" refers to a substantially water-free oily composition.

While the oily admixture may be a cosmetic composition as such, the cosmetic composition may be obtained, for example, by the following preparation method.

A method for preparing a cosmetic composition involves the steps of:

(I) mixing (a) a silicone surfactant having an HLB value of up to 6, (b) an acrylic-silicone graft copolymer, (c) an oil which is liquid at 25° C., and (d) a coloring pigment to form an oily admixture, and (II) mixing the oily admixture resulting from step (I) with another component.

Step (I) is as described above.

Step (II)

In the case of an emulsified composition, for example, a cosmetic composition may be prepared by previously mixing the oily admixture in a separately prepared oil phase and emulsifying the oil phase and a water phase. Alternatively, a cosmetic composition may be prepared by emulsifying a water phase and an oil phase to form an emulsified base, and blending the oily admixture in the emulsified base. Inversely, a cosmetic composition may be prepared by adding the emulsified base to the oily admixture. In the case of a nonaqueous composition, a cosmetic composition may be prepared by mixing the oily admixture with a separately prepared oily phase. A cosmetic composition may also be prepared by adding the oil phase into the oily admixture.

The cosmetic composition of the invention is not particularly limited as long as it contains essential ingredients. The cosmetic composition is applicable to a variety of products, for example, toners, serums, lotions, creams, hair care products, foundations, primers, beauty balms, concealers, loose powders, cheek colors, lipsticks, eye shadows, eye liners, body makeups, deodorants and the foregoing products endowed with a sun-screening function. The form of the cosmetic composition may be selected from a variety of forms including liquid, cream, solid, paste, gel, mousse, souffle, clay, powder, and spray forms.

In the oily admixture and the cosmetic composition of the invention, components commonly used in cosmetics may be blended insofar as the benefits of the invention are not compromised. Each of the components may be of single type or a combination of two or more types. Some of the components may be selected depending on the type of cosmetic composition, and used in ordinary amounts depending on the type of cosmetic composition. Exemplary components include component (e): an oil phase thickener having a melting point of at least 55° C., component (f): a crosslinked silicone, component (g): powder other than (d), component (h): a surfactant other than (a) and (b), component (i): a film former other than (b), component (j): an aqueous component, component (k): an oil other than components (c) and (e), component (l): a UV blocker, component (m): an aqueous thickener, component (n): an oily thickener other than (e), and component (o): other additives.

[Component (e)]

Component (e) used herein is an oil phase thickener having a melting point of at least 55° C., which is not particularly limited as long as it is commonly used in cosmetics, and may be used alone or in suitable combination of two or more. Component (e) is preferably blended in a cosmetic composition as an additional component other than the oily admixture rather than in the oily admixture.

Examples of the oil phase thickener having a melting point of at least 55° C. include waxes, higher alcohols, higher fatty acids, and fatty acid esters of polysaccharides, having a melting point of at least 55° C. Exemplary of the wax are hydrocarbon waxes such as ceresin, ozokerite, paraffin, synthetic waxes, microcrystalline wax, and polyethylene wax, plant-derived waxes such as carnauba wax, rice wax, rice bran wax, jojoba wax (including extremely hydrogenated jojoba oil), and candelilla wax, and animal-derived waxes such as spermaceti, beeswax, and snow white wax. Exemplary of the higher alcohol are cetyl alcohol, stearyl alcohol, arachyl alcohol, and behenyl alcohol. Exemplary of the higher fatty acid are palmitic acid, stearic acid, arachidic acid, and behenic acid. Exemplary of the fatty acid ester of polysaccharide are dextrin palmitate, inulin stearate, sucrose palmitate, and fructooligosaccharide 2-ethylhexanoate. Inter alia, the hydrocarbon waxes are preferred, with ceresin being more preferred.

When used, the amount of component (e) blended is preferably 0.1 to 30% by weight, more preferably 1 to 10% by weight, even more preferably 5 to 15% by weight of the cosmetic composition, though not particularly limited.

[Component (f)]

Component (f) used herein is a crosslinked silicone. Typical of the crosslinked silicone are partially crosslinked methylpolysiloxanes, partially crosslinked polyether-modified silicones, and partially crosslinked polyglycerin-modified silicones. Examples thereof include KSG-210, 240, 310, 320, 330, 340, 320Z, 350Z, 710, 810, 820, 830, 840, 820Z, 850Z, 15, 1510, 16, 1610, 18A, 19, 41A, 42A, 43, 44, 042Z, 045Z, and 048Z, by Shin-Etsu Chemical Co., Ltd.

When used, the amount of component (f) blended is preferably 0.1 to 25% by weight, more preferably 0.2 to 20% by weight, even more preferably 0.5 to 15% by weight, calculated as solids, of the cosmetic composition, though not particularly limited.

[Component (g)]

Component (g) used herein is a powder other than component (d), which is not particularly limited as long as it is commonly used in cosmetics. Examples of component (g) include talc, mica, cericite, barium sulfate, synthetic phlogopite, calcium carbonate, PMMA, nylon powder, crystalline cellulose, crosslinked silicone powders (e.g., KMP-598 and KSG-016F by Shin-Etsu Chemical Co., Ltd.), silicone resins (e.g., KMP-590 and 591 by Shin-Etsu Chemical Co., Ltd.), and silicone resin-coated silicone rubber powders (e.g., KSP-100, 101, 102, 105, 300, 411, and 441 by Shin-Etsu Chemical Co., Ltd.).

When used, the amount of component (g) blended is preferably 0.1 to 90% by weight, more preferably 1 to 35% by weight of the cosmetic composition, though not particularly limited.

[Component (h)]

Component (h) used herein is a surfactant other than components (a) and (b). The surfactant is not particularly limited as long as it is commonly used in cosmetics while suitable surfactants include nonionic, anionic, cationic and ampholytic surfactants. Of these surfactants, preferred are linear or branched polyoxyethylene-modified organopolysiloxanes, linear or branched polyoxyethylenepolyoxypropylene-modified organopolysiloxanes, linear or branched polyoxyethylene/alkyl-co-modified organopolysiloxanes, linear or branched polyoxyethylenepolyoxypropylene/alkyl-co-modified organopolysiloxanes, linear or branched polyglycerin-modified organopolysiloxanes, and linear or branched polyglycerin/alkyl-co-modified organopolysiloxanes, having a HLB value in excess of 6. In these surfactants, the content of hydrophilic polyoxyethylene group, polyoxyethylenepolyoxypropylene group or polyglycerin residue is preferably 10 to 70% by weight of the molecule. Examples of the surfactant other than component (a) include KF-6011, 6013, 6043, and 6100 by Shin-Etsu Chemical Co., Ltd.

When used, the amount of component (h) blended is preferably 0.1 to 15% by weight, more preferably 0.1 to 5% by weight of the cosmetic composition, though not particularly limited.

[Component (i)]

Component (i) used herein is a film former other than (b), which is not particularly limited as long as it is commonly used in cosmetics. Examples of component (i) include latexes such as polyvinyl alcohol, polyvinyl pyrrolidone, polyvinyl acetate, and poly(alkyl acrylates), cellulose derivatives such as dextrin, alkyl celluloses, and nitrocellulose, silicone-modified polysaccharides such as pullulan tri(trimethylsiloxy)silylpropylcarbamate, silicone resins such as trimethylsiloxysilicic acid, silicone based resins such as silicone-modified polynorbornene and fluorine-modified silicone resins, fluoroplastics, aromatic hydrocarbon resins, polymer emulsion resins, terpene based resins, polybutene, polyisoprene, alkyd resins, polyvinyl pyrrolidone-modified polymers, rosin-modified resins, and polyurethane.

Of these, silicone-based film formers are preferred. Preferred examples include, but are not limited to, pullulan tri(trimethylsiloxy)silylpropylcarbamate (commercially available in solution form as TSPL-30-D5, ID by Shin-Etsu Chemical Co., Ltd.), trimethylsiloxysilicic acid (commercially available in solution form as KF-7312J and X-21-5250 by Shin-Etsu Chemical Co., Ltd.), silicone-modified polynorbornene (commercially available in solution form as NBN-30-ID by Shin-Etsu Chemical Co., Ltd.), and organosiloxane grafted polyvinyl alcohol polymers. The film former may be used alone or in admixture.

When used, the amount of component (i) blended is preferably 0.1 to 15% by weight, more preferably 0.1 to 5% by weight, calculated as solids, of the cosmetic composition, though not particularly limited.

[Component (j)]

Component (j) is an aqueous component, which is not particularly limited as long as it is commonly used in cosmetics. Examples of component (j) include water and humectants.

Examples of water include purified water commonly used in cosmetics, sea water, spring water, peat water, and distilled water from fruits and plants. When used, the amount of water blended is preferably 5 to 70% by weight of the cosmetic composition, though not particularly limited.

Suitable humectants include lower alcohols such as ethanol and isopropanol; sucrose alcohols such as sorbitol, maltose and xylitol; polyhydric alcohols such as butylene glycol, dibutylene glycol, propylene glycol, dibutylene glycol, pentylene glycol, decane diol, octane diol, hexane diol, erythritol, glycerin, diglycerin, and polyethylene glycol; glucose, glyceryl glucoside, betaine, hyaluronic acid, chondroitin sulfate, pyrrolidone carboxylate, polyoxyethylene methyl glucoside, and polyoxypropylene methyl glucoside. When used, the amount of the humectant blended is preferably 1 to 30% by weight of the cosmetic composition, though not particularly limited.

[Component (k)]

Component (k) used herein is an oil other than components (c) and (e), which is not particularly limited as long as it is commonly used in cosmetics. Examples include plant fats and oils such as shea butter, cacao butter and astrocaryum murumuru seed butter, fatty acids such as lauric acid and myristic acid, and white vaseline.

When used, the amount of component (k) blended is preferably 0.1 to 15% by weight of the cosmetic composition, though not particularly limited.

[Component (l)]

Component (l) used herein is a UV blocking agent, which is not particularly limited as long as it is commonly used in cosmetics. Typical of component (l) are UV absorbers and UV scattering agents. Examples of the UV absorber include homomenthyl salicylate, octocrylene, 4-tert-butyl-4'-methoxydibenzoyl methane, 4-(2-β-glucopyranosiloxy) propoxy-2-hydroxybenzophenone, octyl salicylate, hexyl 2-[4-(diethylamino)-2-hydroxybenzoyl]benzoate, dihydroxydimethoxybenzophenone, sodium dihydroxydimethoxybenzophenonedisulfonate, dihydroxybenzophenone, dimethico-diethylbenzal-malonate, 1-(3,4-dimethoxyphenyl)-4,4-dimethyl-1,3-pentanedione, 2-ethylhexyl dimethoxybenzylidene dioxoimidazolidine propionate, tetrahydroxybenzophenone, terephthalylidene dicamphor sulfonic acid, 2,4,6-tris[4-(2-ethylhexyloxycarbonyl)anilino]-1,3,5-triazine, methylbis(trimethylsiloxy)silylisopentyl trimethoxycinnamate, drometrizole trisiloxane, 2-ethylhexyl p-dimethylaminobenzoate, isopropyl p-methoxycinnamate, 2-ethylhexyl p-methoxycinnamate, 2,4-bis[{4-(2-ethylhexyloxy)-2-hydroxy}-phenyl]-6-(4-methoxyphenyl)-1,3,5-triazine, 2-hydroxy-4-methoxybenzophenone, hydroxymethoxybenzophenone sulfonic acid and trihydrate thereof, hydroxymethoxybenzophenone sodium sulfonate, phenylbenzimidazole sulfonic acid, and 2,2'-methylenebis [6-(2H-benzotriazol-2-yl)-4-(1,1,3,3-tetramethylbutyl)phenol]. A mixture of a UVA absorber (e.g., hexyl diethylaminohydroxybenzoylbenzoate) and a UVB absorber (e.g., ethylhexyl methoxycinnamate) may also be used.

When used, the amount of the UV absorber blended is preferably 0.1 to 20% by weight of the cosmetic composition, though not particularly limited.

As the UV scattering agent, metal oxides in microparticulate form are suitable, for example, zinc oxide, titanium oxide, iron oxide, cerium oxide, and tungsten oxide. The UV scattering agent may be used along with the UV absorber.

When used, the amount of the UV scattering agent blended is preferably 0.1 to 20% by weight of the cosmetic composition, though not particularly limited.

[Component (m)]

Component (m) used herein is an aqueous thickener, which is not particularly limited as long as it is commonly used in cosmetics. Examples thereof include fermented high-molecular-weight compounds such as hyaluronic acid and salts thereof; naturally occurring high-molecular-weight compounds such as gum arabic, guar gum, carrageenan, agar, quince seed, locust bean gum, xanthan gum, and pullulan; celluloses such as hydroxyethyl cellulose and hydroxypropylmethyl cellulose; vinyl based polymers such as carboxyvinyl polymers; acrylic polymers such as acryloyldimethyltaurine ammonium/VP copolymers, sodium acrylate/sodium acryloyldimethyltaurine copolymers, hydroxyethyl acrylate/sodium acryloyldimethyltaurine copolymers and polyacrylamide; and inorganic powders such as bentonite and hectorite.

[Component (n)]

Component (n) used herein is an oily thickener other than component (e), which is not particularly limited as long as it is commonly used in cosmetics. Examples thereof include hydrophobized microparticulate silica such as silylated silica, metal soaps such as aluminum stearate, and organic-modified clay minerals such as disteardimonium hectorite, stearalkonium hectorite, and hectorite.

When used, the amount of component (n) blended is preferably 0.1 to 5.0% by weight of the cosmetic composition, though not particularly limited.

[Component (o)]

Other additives include antiperspirants, preservatives, bactericides, perfuming agents, salts, antioxidants, pH adjusting agents, chelating agents, refreshing agents, anti-inflammatory agents, brightening agents (e.g., whitening agents, cell activating agents, rough skin modifiers, blood flow enhancing agents, skin astringents, and anti-seborrheic agents), vitamins, amino acids, water-soluble polymers, fibers, and inclusion compounds.

EXAMPLES

Examples and Comparative Examples are given below for further illustrating the invention although the invention is not limited thereto. In the following Examples, compositional "%" refers to % by weight unless otherwise stated. Some components are expressed by INCI names.

Examples and Comparative Examples

Cosmetic compositions of the formulation shown in the following Tables were prepared by the following method and evaluated for properties by the following tests.

(1) Property Evaluation

The cosmetic compositions of Examples and Comparative Examples were evaluated for degree and color of uneven pigment distribution in the cosmetic composition in bulk. The degree of uneven pigment distribution was evaluated by a panel of ten panelists. Evaluation was made according to the criterion shown in Table 1. The result was judged according to the following judgment criterion based on the average point of ten panelists. The results are shown in Tables 2 to 4.

TABLE 1

| Point | Degree of uneven pigment distribution |
|---|---|
| 5 | good |
| 4 | rather good |
| 3 | ordinary |
| 2 | rather poor |
| 1 | poor |

(2) Judgment Criterion

⊚: average point≥4.0
○: 3.0≤average point <4.0
Δ: 2.0≤average point <3.0
×: average point<2.0

Examples 1 to 11 and Comparative Examples 1 to 4

Solid W/O emulsion cosmetic compositions of the formulation shown in Tables 2 to 4 were prepared and evaluated for properties. The blended amounts are amounts of components in the described product whereas blending weight ratios represented by (b)/(a) and {(a)+(b)}/(d) are based on the net weight of components.

<Preparation of Oily Admixture>

An oily admixture (1) is prepared by

A: mixing all components on a dispersing mixer until uniform, and

B: mixing and dispersing A on a three-roll mill.

<Preparation of Cosmetic Composition>

A cosmetic composition is prepared by

C: heating and melting an oil phase (2), adding oily admixture (1) thereto, and mixing until uniform, D: heating and melting a water phase (3) and mixing until uniform, E: adding D to C and heating and emulsifying, F: vacuum defoaming E, filling a container with E, and cooling.

TABLE 2

| | Components (%) | Example 1 | Example 2 | Example 3 | Example 4 | Comparative Example 1 | Comparative Example 2 | Comparative Example 3 |
|---|---|---|---|---|---|---|---|---|
| (1) Oily admixture | (a) branched polyglycerin/alkyl-co-modified organopolysiloxane (*1) | 0.25 | 0.15 | 0.1 | 0.3 | — | 0.4 | — |
| | (b) acrylate/ethylhexyl acrylate/dimethicone methacrylate copolymer (*2) | 0.15 | 0.25 | 0.3 | 0.1 | — | — | 0.4 |
| | (c) isotridecyl isononanoate | 2 | 2 | 2 | 2 | 2.4 | 2 | 2 |
| | (d) silicone-treated titanium oxide (*3) | 8.5 | 8.5 | 8.5 | 8.5 | 8.5 | 8.5 | 8.5 |
| | (d) silicone-treated yellow iron oxide (*4) | 1 | 1 | 1 | 1 | 1 | 1 | 1 |
| | (d) silicone-treated red iron oxide (*5) | 0.4 | 0.4 | 0.4 | 0.4 | 0.4 | 0.4 | 0.4 |
| | (d) silicone-treated black iron oxide (*6) | 0.1 | 0.1 | 0.1 | 0.1 | 0.1 | 0.1 | 0.1 |
| (2) Oil phase | branched polyglycerin/alkyl-co-modified organopolysiloxane (*1) | 1.5 | 1.5 | 1.5 | 1.5 | 1.5 | 1.5 | 1.5 |
| | partially crosslinked polyglycerin/alkyl-co-modified silicone composition (*7) | 5 | 5 | 5 | 5 | 5 | 5 | 5 |
| | partially crosslinked phenyl-modified silicone composition (*8) | 3 | 3 | 3 | 3 | 3 | 3 | 3 |
| | cyclopentasiloxane | 8 | 8 | 8 | 8 | 8 | 8 | 8 |
| | diphenylsiloxyphenyl trimethicone (*9) | 7.5 | 7.5 | 7.5 | 7.5 | 7.5 | 7.5 | 7.5 |
| | (e) ceresin | 5 | 5 | 5 | 5 | 5 | 5 | 5 |
| (3) Water phase | BG | 6 | 6 | 6 | 6 | 6 | 6 | 6 |
| | glycerin | 5.5 | 5.5 | 5.5 | 5.5 | 5.5 | 5.5 | 5.5 |
| | Na citrate | 0.2 | 0.2 | 0.2 | 0.2 | 0.2 | 0.2 | 0.2 |
| | Na chloride | 1 | 1 | 1 | 1 | 1 | 1 | 1 |
| | phenoxyethanol | 0.3 | 0.3 | 0.3 | 0.3 | 0.3 | 0.3 | 0.3 |
| | purified water | balance | balance | balance | balance | balance | balance | balance |
| | Total | 100 | 100 | 100 | 100 | 100 | 100 | 100 |
| | (b)/(a) | 0.6 | 1.667 | 3 | 0.333 | — | — | — |
| | {(a) + (b)}/(d) | 0.04 | 0.04 | 0.04 | 0.04 | — | 0.04 | 0.04 |
| Property evaluation | Degree of uneven pigment distribution | ◎ | ○ | ○ | ◎ | X | Δ | X |
| | Color of uneven pigment distribution | colorless | red | red | colorless | red | white | red |

The notes in Tables 2 to 4 are as follows.
(*1) lauryl polyglyceryl-3 polydimethylsiloxyethyl dimethicone: KF-6105 (by Shin-Etsu Chemical Co., Ltd.)
(*2) KP-578 (by Shin-Etsu Chemical Co., Ltd.)
(*3) KTP-09W (by Shin-Etsu Chemical Co., Ltd.)
(*4) KTP-09Y (by Shin-Etsu Chemical Co., Ltd.)
(*5) KTP-09R (by Shin-Etsu Chemical Co., Ltd.)
(*6) KTP-09B (by Shin-Etsu Chemical Co., Ltd.)
(*7) KSG-830 (by Shin-Etsu Chemical Co., Ltd.)
(*8) KSG-18A (by Shin-Etsu Chemical Co., Ltd.)
(*9) KJF-56A (by Shin-Etsu Chemical Co., Ltd.)

As is evident from Table 2, the cosmetic compositions of Examples 1 to 4 within the scope of the invention eliminated uneven pigment distribution and developed uniform color. In contrast, Comparative Examples 1 to 3 in which either one of components (a) and (b) was omitted from the oily admixture showed outstandingly uneven pigment distribution. It is demonstrated that the combined use of components (a) and (b) exerts a significant effect of improving uneven pigment distribution.

TABLE 3

| | Components (%) | Example 5 | Example 6 | Example 7 |
|---|---|---|---|---|
| (1) Oily admixture | (a) branched polyglycerin/alkyl-co-modified organopolysiloxane (*1) | 0.125 | 0.375 | 0.5 |
| | (b) acrylate/ethylhexyl acrylate/dimethicone methacrylate copolymer (*2) | 0.075 | 0.225 | 0.3 |
| | (c) isotridecyl isononanoate | 2.4 | 1.8 | 1.6 |
| | (d) silicone-treated titanium oxide (*3) | 8.5 | 8.5 | 8.5 |
| | (d) silicone-treated yellow iron oxide (*4) | 1 | 1 | 1 |
| | (d) silicone-treated red iron oxide (*5) | 0.4 | 0.4 | 0.4 |
| | (d) silicone-treated black iron oxide (*6) | 0.1 | 0.1 | 0.1 |
| (2) Oil phase | branched polyglycerin/alkyl-co-modified organopolysiloxane (*1) | 1.5 | 1.5 | 1.5 |
| | partially crosslinked polyglycerin/alkyl-co-modified silicone composition (*7) | 5 | 5 | 5 |
| | partially crosslinked phenyl-modified silicone composition (*8) | 3 | 3 | 3 |
| | cyclopentasiloxane | 8 | 8 | 8 |
| | diphenylsiloxyphenyl trimethicone (*9) | 7.5 | 7.5 | 7.5 |
| | (e) ceresin | 5 | 5 | 5 |
| (3) Water phase | BG | 6 | 6 | 6 |
| | glycerin | 5.5 | 5.5 | 5.5 |
| | Na citrate | 0.2 | 0.2 | 0.2 |
| | Na chloride | 1 | 1 | 1 |
| | phenoxyethanol | 0.3 | 0.3 | 0.3 |
| | purified water | balance | balance | balance |
| | Total | 100 | 100 | 100 |
| | (b)/(a) | 0.6 | 0.6 | 0.6 |
| | {(a) + (b)}/(d) | 0.02 | 0.06 | 0.08 |
| Property evaluation | Degree of uneven pigment distribution | ○ | ◎ | ○ |
| | Color of uneven pigment distribution | white | colorless | red |

Table 3 tabulates the examples wherein the ratio of component (b) to component (a) in the oily admixture is fixed while the weight ratio of the sum of components (a) and (b) to component (d) is varied. Examples 5 to 7 are suppressed in uneven pigment distribution as compared with Comparative Examples 1 to 3. Especially, Example 6 gave a cosmetic composition devoid of uneven pigment distribution and developing uniform color.

amount of the branched polyglycerin/alkyl-co-modified organopolysiloxane is blended as component (a) in the oily admixture as in Example 11.

As is evident from the results in Tables 2 to 4, a cosmetic composition which is uniform due to suppression of uneven pigment distribution is obtained by forming an oily admix-

TABLE 4

| | Components (%) | Example 8 | Example 9 | Comparative Example 4 | Example 10 | Example 11 |
|---|---|---|---|---|---|---|
| (1) Oily admixture | (a) branched polyglycerin/alkyl-co-modified organopolysiloxane (*1) | 1.75 | 1.5 | — | 0.25 | 3.25 |
| | (b) acrylate/ethylhexyl acrylate/dimethicone methacrylate copolymer (*2) | 0.15 | 0.15 | 0.15 | 0.15 | 0.15 |
| | (c) isotridecyl isononanoate | 2 | 2 | 2 | 2 | 2 |
| | (d) silicone-treated titanium oxide (*3) | 8.5 | 8.5 | 8.5 | 8.5 | 8.5 |
| | (d) silicone-treated yellow iron oxide (*4) | 1 | 1 | 1 | 1 | 1 |
| | (d) silicone-treated red iron oxide (*5) | 0.4 | 0.4 | 0.4 | 0.4 | 0.4 |
| | (d) silicone-treated black iron oxide (*6) | 0.1 | 0.1 | 0.1 | 0.1 | 0.1 |
| (2) Oil phase | branched polyglycerin/alkyl-co-modified organopolysiloxane (*1) | — | 0.25 | 1.75 | 3 | — |
| | partially crosslinked polyglycerin/alkyl-co-modified silicone composition (*7) | 5 | 5 | 5 | 5 | 5 |
| | partially crosslinked phenyl-modified silicone composition (*8) | 3 | 3 | 3 | 3 | 3 |
| | cyclopentasiloxane | 8 | 8 | 8 | 8 | 8 |
| | diphenylsiloxyphenyl trimethicone (*9) | 7.5 | 7.5 | 7.5 | 7.5 | 7.5 |
| | (e) ceresin | 5 | 5 | 5 | 5 | 5 |
| (3) Water phase | BG | 6 | 6 | 6 | 6 | 6 |
| | glycerin | 5.5 | 5.5 | 5.5 | 5.5 | 5.5 |
| | Na citrate | 0.2 | 0.2 | 0.2 | 0.2 | 0.2 |
| | Na chloride | 1 | 1 | 1 | 1 | 1 |
| | phenoxyethanol | 0.3 | 0.3 | 0.3 | 0.3 | 0.3 |
| | purified water | balance | balance | balance | balance | balance |
| | Total | 100 | 100 | 100 | 100 | 100 |
| | (b)/(a) | 0.086 | 0.1 | — | 0.6 | 0.046 |
| | {(a) + (b)}/(d) | 0.19 | 0.17 | 0.02 | 0.04 | 0.34 |
| Property evaluation | Degree of uneven pigment distribution | ◯ | ◯ | X | ◎ | ◯ |
| | Color of uneven pigment distribution | red | red | red | colorless | red |

In Example 8 in Table 4, the branched polyglycerin/alkyl-co-modified organopolysiloxane, which was blended in the oil phase as an emulsifier in Example 1, was entirely blended as component (a) in the oily admixture. In Example 9, a cosmetic composition was obtained by exchanging the amount of component (a), branched polyglycerin/alkyl-co-modified organopolysiloxane in the oily admixture with the amount of the same component in the oil phase in Example 1. In Comparative Example 4, the branched polyglycerin/alkyl-co-modified organopolysiloxane was not blended as component (a) in the oily admixture, but all blended in the oil phase. Examples 8 and 9 were minimized in uneven pigment distribution and good in emulsion state whereas Comparative Example 4 showed outstanding uneven pigment distribution. As is evident from these results, the benefits of the invention are attained even when a cosmetic composition was prepared by blending the branched polyglycerin/alkyl-co-modified organopolysiloxane (to be blended for the emulsifier purpose) as component (a) in the oily admixture. However, even when the same amount of the branched polyglycerin/alkyl-co-modified organopolysiloxane is blended in a cosmetic composition as in Comparative Example 4, the desired benefits are not obtained if not blended in the oily admixture. Also, uneven pigment distribution is suppressed when a large amount of the branched polyglycerin/alkyl-co-modified organopolysiloxane is blended as an emulsifier as in Example 10, and when a large ture in which a coloring pigment is previously dispersed in an oil which is liquid at 25° C., using a silicone surfactant having a HLB value of up to 6 and an acrylic silicone graft copolymer in combination, and blending the oily admixture in a cosmetic composition.

Example 12

W/O Liquid Foundation
A W/O liquid foundation was obtained by
A: mixing components (1) to (7) on a three-roll mill to form an oily admixture,
B: uniformly mixing A and (8) to (15),
C: uniformly mixing components (16) to (20), and
D: adding C to B, followed by emulsification.

| Formulation | (%) |
|---|---|
| (1) branched polyoxyethylene-modified organopolysiloxane (*10) | 0.3 |
| (2) acrylate/dimethicone copolymer composition (*11) | 1.0 |
| (3) dimethylpolysiloxane (6 cs) | 1.5 |
| (4) silicone-treated titanium oxide (*12) | 8.5 |
| (5) silicone-treated yellow iron oxide (*12) | 1.0 |
| (6) silicone-treated red iron oxide (*12) | 0.4 |
| (7) silicone-treated black iron oxide (*12) | 0.1 |
| (8) partially crosslinked poly oxyethylene-modified silicone composition (*13) | 3.0 |

| Formulation | (%) |
| --- | --- |
| (9) crosslinked dimethylpolysiloxane composition (*14) | 7.0 |
| (10) linear polyoxyethylene-modified organopolysiloxane (*15) | 1.0 |
| (11) cyclopentasiloxane | balance |
| (12) dimethylpolysiloxane (10 cs) | 8.0 |
| (13) organic modified clay mineral | 0.5 |
| (14) isotridecyl isononanoate | 5.0 |
| (15) silicone resin-coated alkyl-modified silicone rubber powder (*16) | 2.0 |
| (16) 1,3-butylene glycol | 5.0 |
| (17) phenoxyethanol | 0.2 |
| (18) sodium citrate | proper |
| (19) magnesium sulfate | proper |
| (20) purified water | 32.0 |
| Total | 100.0 |

(*10) KF-6028 (by Shin-Etsu Chemical Co., Ltd.)
(*11) KP-545 (by Shin-Etsu Chemical Co., Ltd.)
(*12) treated with KF-99P (by Shin-Etsu Chemical Co., Ltd.)
(*13) KSG-210 (by Shin-Etsu Chemical Co., Ltd.)
(*14) KSG-15 (by Shin-Etsu Chemical Co., Ltd.)
(*15) KF-6017 (by Shin-Etsu Chemical Co., Ltd.)
(*16) KSP-441 (by Shin-Etsu Chemical Co., Ltd.)

Viscosity measuring conditions: Brookfield viscometer, spindle LV-4, 60 seconds after 6 revolutions
Initial viscosity: 8,900 mPa·s
Viscosity after 50° C./1 month: 9,700 mPa·s The resulting W/O liquid foundation had a low viscosity and was free of uneven pigment distribution and fully uniform in both appearance color and coating color despite a high loading of pigments.

Example 13

W/O Cream Foundation

A W/O cream foundation was obtained by
A: mixing components (1) to (8) on a three-roll mill to form an oily admixture,
B: uniformly mixing A and (9) to (18),
C: uniformly mixing components (19) to (24), and
D: adding C to B, followed by emulsification.

| Formulation | (%) |
| --- | --- |
| (1) branched polyglycerin-modified organopolysiloxane (*17) | 0.6 |
| (2) acrylate/ethylhexyl acrylate/dimethicone methacrylate copolymer (*2) | 0.4 |
| (3) triethylhexanoin | 7.0 |
| (4) silicone-treated titanium oxide (*18) | 8.5 |
| (5) silicone-treated yellow iron oxide (*18) | 1.0 |
| (6) silicone-treated red iron oxide (*18) | 0.4 |
| (7) silicone-treated black iron oxide (*18) | 0.1 |
| (8) metal soap-treated microparticulate titanium oxide (UV scattering agent) | 10 |
| (9) partially crosslinked, branched polyoxyethylene/alkyl-co-modified silicone composition (*19) | 3.0 |
| (10) partially crosslinked, branched alkyl-modified dimethylpolysiloxane composition (*20) | 7.0 |
| (11) linear polyoxyethylene-polyoxypropylene/alkyl-co-modified organopolysiloxane (*21) | 1.5 |
| (12) cyclopentasiloxane | balance |
| (13) ethylhexyl methoxycinnamate | 4.0 |
| (14) hexyl diethylaminohydroxybenzoylbenzoate | 1.0 |
| (15) organic modified clay mineral | 1.2 |
| (16) isotridecyl isononanoate | 7.0 |
| (17) diphenylsiloxyphenyl trimethicone (*9) | 7.0 |
| (18) trimethylsiloxysilicic acid composition (*22) | 1.0 |
| (19) silicone resin-coated phenyl-modified silicone rubber powder (*23) | 1.0 |
| (20) dipropylene glycol | 4.0 |
| (21) phenoxyethanol | 0.2 |
| (22) sodium citrate | proper |
| (23) magnesium sulfate | proper |
| (24) purified water | 30.0 |
| Total | 100.0 |

(*17) KF-6106 (by Shin-Etsu Chemical Co., Ltd.)
(*18) treated with AES-3083 (by Shin-Etsu Chemical Co., Ltd.)
(*19) KSG-350Z (by Shin-Etsu Chemical Co., Ltd.)
(*20) KSG-45Z (by Shin-Etsu Chemical Co., Ltd.)
(*21) KF-6048 (by Shin-Etsu Chemical Co., Ltd.)
(*22) KF-7312J (by Shin-Etsu Chemical Co., Ltd.)
(*23) KSP-300 (by Shin-Etsu Chemical Co., Ltd.)

The resulting W/O cream foundation was free of uneven pigment distribution and fully uniform in both appearance color and coating color despite a high loading of pigments.

Example 14

O/W Cream Foundation

An O/W cream foundation was obtained by
A: mixing components (1) to (7) on a three-roll mill to form an oily admixture,
B: uniformly mixing A, (8) and (9),
C: uniformly mixing components (10) to (17), and
D: adding B to C, followed by emulsification.

| Formulation | (%) |
| --- | --- |
| (1) branched polyglycerin-modified organopolysiloxane (*24) | 0.3 |
| (2) acrylate/ethylhexyl acrylate/dimethicone methacrylate copolymer (*2) | 0.1 |
| (3) dimethylpolysiloxane (6 cs) | 2.0 |
| (4) silicone-treated titanium oxide (*25) | 8.5 |
| (5) silicone-treated yellow iron oxide (*25) | 1.0 |
| (6) silicone-treated red iron oxide (*25) | 0.4 |
| (7) silicone-treated black iron oxide (*25) | 0.1 |
| (8) cyclopentasiloxane | 6.0 |
| (9) dimethylpolysiloxane (20 cs) | 6.0 |
| (10) acrylate/$C_{10-30}$ alkyl acrylate cross-polymer (*26) | 0.2 |
| (11) aqueous solution of acrylamide/sodium acryloyldimethyltaurine copolymer/isohexadecane/polysolbate 80 (*27) | 1.2 |
| (12) potassium hydroxide (1% aqueous solution) | 8.0 |
| (13) 1,3-butylene glycol | 5.0 |
| (14) glycerin | 5.0 |
| (15) ethanol | 5.0 |
| (16) phenoxyethanol | 0.4 |
| (17) purified water | balance |
| Total | 100.0 |

(*24) KF-6104 (by Shin-Etsu Chemical Co., Ltd.)
(*25) treated with KF-9908 (by Shin-Etsu Chemical Co., Ltd.)
(*26) Pemulen TR-1 (by Lubrizol Advanced Materials)
(*27) Simulge 1600 (by Seppic)

The resulting O/W cream foundation having the pigments dispersed in the inner oil phase was free of uneven pigment distribution and fully uniform in both appearance color and coating color.

Example 15

Nonaqueous Solid Foundation

A nonaqueous solid foundation was obtained by
A: mixing components (1) to (7) on a three-roll mill to form an oily admixture,
B: heating and uniformly mixing A and (8) to (17), and
C: filling a container with B, followed by cooling.

| Formulation | (%) |
|---|---|
| (1) branched polyoxyethylene/alkyl-co-modified organopolysiloxane (*28) | 0.3 |
| (2) acrylate/dimethicone copolymer solution (*29) | 1.0 |
| (3) mineral oil | 2.4 |
| (4) silicone-treated titanium oxide (*30) | 8.5 |
| (5) silicone-treated yellow iron oxide (*30) | 1.0 |
| (6) silicone-treated red iron oxide (*30) | 0.4 |
| (7) silicone-treated black iron oxide (*30) | 0.1 |
| (8) isotridecyl isononanoate | balance |
| (9) dimethylpolysiloxane (6 cs) | 4.0 |
| (10) diphenylsiloxyphenyl trimethicone (*9) | 7.5 |
| (11) squalane | 5.0 |
| (12) silicone resin-coated silicone rubber powder (*31) | 12.0 |
| (13) polymethylsilsesquioxane (*32) | 4.0 |
| (14) partially crosslinked dimethylpolysiloxane (*33) | 7.0 |
| (15) branched polyoxyethylene/alkyl-co-modified organopolysiloxane (*28) | 0.5 |
| (16) dextrin palmitate | 8.5 |
| (17) metal soap-treated microparticulate titanium oxide dispersion as UV scattering agent (*34) | 18.0 |
| Total | 100.0 |

(*28) KF-6038 (by Shin-Etsu Chemical Co., Ltd.)
(*29) KP-550 (by Shin-Etsu Chemical Co., Ltd.)
(*30) treated with KF-9901 (by Shin-Etsu Chemical Co., Ltd.)
(*31) KSP-101 (by Shin-Etsu Chemical Co., Ltd.)
(*32) KMP-591 (by Shin-Etsu Chemical Co., Ltd.)
(*33) KSG-16 (by Shin-Etsu Chemical Co., Ltd.)
(*34) SPD-T7 (by Shin-Etsu Chemical Co., Ltd.)

The resulting nonaqueous solid foundation was free of uneven pigment distribution upon filling and fully uniform in both appearance color and coating color.

Example 16

W/O Primer Cream

A W/O primer cream was obtained by
A: mixing components (1) to (8) on a paint shaker (media diameter 1.5 mm) to form an oily admixture,
B: uniformly mixing A and (9) to (18),
C: uniformly mixing components (19) to (23), and
D: adding C to B, followed by emulsification.

| Formulation | (%) |
|---|---|
| (1) branched polyglycerin-modified organopolysiloxane (*17) | 0.4 |
| (2) acrylate/ethylhexyl acrylate/dimethicone methacrylate copolymer (*2) | 0.3 |
| (3) cyclopentasiloxane | 7.5 |
| (4) acrylic silicone-treated titanium oxide (*35) | 1.0 |
| (5) acrylic silicone-treated yellow iron oxide (*35) | 0.1 |
| (6) acrylic silicone-treated red iron oxide (*35) | 0.04 |
| (7) acrylic silicone-treated black iron oxide (*35) | 0.01 |
| (8) metal soap-treated microparticulate titanium oxide as UV scattering agent | 5.0 |
| (9) partially crosslinked polyoxyethylene/alkyl-co-modified silicone composition (*36) | 3.0 |
| (10) partially crosslinked alkyl-modified dimethylpolysiloxane composition (*37) | 3.0 |
| (11) branched polyoxyethylene-modified organopolysiloxane (*38) | 2.0 |
| (12) diphenylsiloxyphenyl trimethicone (*9) | 5.0 |
| (13) ethylhexyl methoxycinnamate | 7.0 |
| (14) octocrylene | 3.0 |
| (15) hexyl diethylaminohydroxybenzoylbenzoate | 3.0 |
| (16) acrylate/dimethicone copolymer solution (*11) | 1.0 |
| (17) silicone-treated microparticulate zinc oxide dispersion as UV scattering agent (*39) | 10.0 |
| (18) BHT | 0.1 |
| (19) ethanol | 8.0 |
| (20) glycerin | 5.0 |
| (21) sodium citrate | 0.5 |
| (22) phenoxyethanol | 0.3 |
| (23) purified water | balance |
| Total | 100.0 |

(*35) treated with KP-574 (by Shin-Etsu Chemical Co., Ltd.)
(*36) KSG-330 (by Shin-Etsu Chemical Co., Ltd.)
(*37) KSG-43 (by Shin-Etsu Chemical Co., Ltd.)
(*38) KF-6028 (by Shin-Etsu Chemical Co., Ltd.)
(*39) SPD-Z5 (by Shin-Etsu Chemical Co., Ltd.)

The resulting W/O primer cream was smooth, outstandingly spreadable, free of uneven pigment distribution, and fully uniform in both appearance color and coating color.

Example 17

Nonaqueous Concealer

A nonaqueous concealer was obtained by
A: mixing components (1) to (7) on a three-roll mill to form an oily admixture, and
B: uniformly mixing A and components (8) to (13).

| Formulation | (%) |
|---|---|
| (1) linear polyoxyethylene-modified organopolysiloxane (*40) | 0.006 |
| (2) acrylate/ethylhexyl acrylate/dimethicone methacrylate copolymer (*2) | 0.004 |
| (3) triethylhexanoin | 0.1 |
| (4) silicone-treated titanium oxide (*3) | 0.2 |
| (5) silicone-treated yellow iron oxide (*3) | 0.01 |
| (6) silicone-treated red iron oxide (*3) | 0.005 |
| (7) silicone-treated black iron oxide (*3) | 0.001 |
| (8) silicone resin-coated silicone rubber powder (*31) | 23.0 |
| (9) silicone resin-coated phenyl-modified silicone rubber powder (*23) | 5.0 |
| (10) crosslinked dimethylpolysiloxane (*41) | 6.0 |
| (11) dimethylpolysiloxane (6 cs) | 40.0 |
| (12) diphenylsiloxyphenyl trimethicone (*9) | 7.0 |
| (13) decamethylcyclopentasiloxane | balance |
| Total | 100.0 |

(*40) KF-6017 (by Shin-Etsu Chemical Co., Ltd.)
(*41) KSG-19 (by Shin-Etsu Chemical Co., Ltd.)

The resulting nonaqueous concealer had a smooth non-sticky feeling and was free of uneven pigment distribution and fully uniform in both appearance color and coating color.

Example 18

Lipstick
A lipstick was obtained by
A: mixing components (1) to (10) on a three-roll mill to form an oily admixture,
B: heating A and components (11) to (18) at 95° C. and uniformly mixing them, and
C: filling a container with B, and cooling.

| Formulation | (%) |
|---|---|
| (1) branched polyglycerin/alkyl-co-modified organopolysiloxane (*1) | 0.3 |
| (2) acrylate/ethylhexylacrylate/dimethicone methacrylate copolymer (*2) | 0.1 |
| (3) diisostearyl malate | 6.0 |
| (4) Red #201 | 0.3 |
| (5) Red #202 | 0.4 |
| (6) Yellow #4 | 1.2 |
| (7) silicone-treated titanium oxide (*3) | 2.9 |
| (8) silicone-treated black iron oxide (*3) | 0.2 |
| (9) silicone-treated red iron oxide (*3) | 0.7 |
| (10) mica (pearl pigment) | 7.3 |
| (11) candelilla wax | 8.6 |
| (12) polyethylene | 5.0 |
| (13) microcrystalline wax | 0.8 |
| (14) silicone wax (*42) | 8.2 |
| (15) macadamia nut oil | 6.6 |
| (16) isotridecyl isononanoate | 4.5 |
| (17) acrylate/dimethicone copolymer solution (*11) | 4.0 |
| (18) cyclopentasiloxane | balance |
| Total | 100.0 |

(*42) KP-561P (by Shin-Etsu Chemical Co., Ltd.)

The resulting lipstick exhibited a good color development, eliminated uneven pigment and pearl distributions, and was fully uniform in both appearance color and coating color.

The invention claimed is:

1. A cosmetic composition having an oily admixture blended therein, the oily admixture comprising
   (a) a silicone surfactant having an HLB value of up to 6,
   (b) an acrylic silicone graft copolymer,
   (c) an oil which is liquid at 25° C., and
   (d) a coloring pigment,
   wherein the total amount of components (a) to (d) is 40 to 100% by weight based on the oily admixture;
   wherein a blending weight ratio of component (b) to component (a) in the oily admixture, represented by (b)/(a), is from 0.046 to 3, and a blending weight ratio of the sum of components (a) and (b) to component (d) in the oily admixture, represented by $\{(a)+(b)\}/(d)$, is at least 0.02;
   wherein component (a) is a polyglycerin-modified silicone surfactant;
   wherein component (b) is an acrylate/ethylhexyl acrylate/dimethicone methacrylate copolymer (INCI name); and
   wherein component (c) is at least one oil selected from the group consisting of hydrocarbon oils, ester oils, and silicone oils.

2. The cosmetic composition of claim 1 wherein component (a) is a polyglycerin-modified silicone surfactant having an alkyl chain and/or silicone chain branching from a silicone backbone.

3. The cosmetic composition of claim 1 wherein component (d) is a coloring pigment selected from titanium oxide and iron oxide.

4. The cosmetic composition of claim 1 wherein component (d) is a coloring pigment which has been subjected to inorganic surface treatment or hydrophobic surface treatment.

5. The cosmetic composition of claim 4 wherein the inorganic surface treatment is a surface treatment with an inorganic surface treatment agent selected from alumina, aluminum hydroxide, and silica.

6. The cosmetic composition of claim 4 wherein the hydrophobic surface treatment is a surface treatment with a hydrophobic surface treatment agent selected from silicones, fluorine compounds, metal soaps, and amino acids.

7. The cosmetic composition of claim 1, further comprising (e) 1 to 10% by weight based on the cosmetic composition of an oily thickener having a melting point of at least 55° C.

8. The cosmetic composition of claim 1 which is a nonaqueous composition.

9. The cosmetic composition of claim 1 which is an emulsified composition.

10. The cosmetic composition of claim 9 which is of water-in-oil or oil-in-water-in-oil type.

11. A method for preparing a cosmetic composition comprising the steps of:
    (I) mixing the oily admixture of claim 1, and
    (II) mixing the oily admixture resulting from step (I) with another component to form a cosmetic composition.

12. The method of claim 11, wherein the cosmetic composition is an emulsified composition, and
    the step (II) is conducted by:
    (i) previously mixing the oily admixture in a separately prepared oil phase, and emulsifying the oil phase and a water phase;
    (ii) emulsifying a water phase and an oil phase to form an emulsified base, and blending the oily admixture in the emulsified base; or
    (iii) emulsifying a water phase and an oil phase to form an emulsified base, and adding the emulsified base to the oily admixture.

13. The method of claim 11, wherein the cosmetic composition is a nonaqueous composition, and
    the step (II) is conducted by:
    (iv) mixing the oily admixture with a separately prepared oily phase; or
    (v) adding the oil phase into the oily admixture.

* * * * *